(12) United States Patent
Verneau

(10) Patent No.: US 7,892,582 B2
(45) Date of Patent: Feb. 22, 2011

(54) COMPOSITION FOR ORAL ADMINISTRATION CONTAINING CAPSAICINOIDS

(75) Inventor: Bernadette Verneau, Frejus (FR)

(73) Assignee: Institut Phytoceutic, Frejus (FR)

( * ) Notice: Subject to any disclaimer, the term of this patent is extended or adjusted under 35 U.S.C. 154(b) by 459 days.

(21) Appl. No.: 10/542,406

(22) PCT Filed: Jan. 16, 2004

(86) PCT No.: PCT/FR2004/000085

§ 371 (c)(1),
(2), (4) Date: Mar. 29, 2006

(87) PCT Pub. No.: WO2004/064542

PCT Pub. Date: Aug. 5, 2004

(65) Prior Publication Data

US 2007/0141184 A1    Jun. 21, 2007

(30) Foreign Application Priority Data

Jan. 17, 2003    (FR)    .................................. 03 00506

(51) Int. Cl.
*A61K 36/00* (2006.01)
*A61K 36/81* (2006.01)
*A61K 36/899* (2006.01)
*A61K 36/48* (2006.01)
*A61K 36/28* (2006.01)
*A61K 47/00* (2006.01)

(52) U.S. Cl. ........................ 424/760; 424/725; 424/757; 424/764; 424/750; 424/776; 514/787

(58) Field of Classification Search .................. None
See application file for complete search history.

(56) References Cited

U.S. PATENT DOCUMENTS

| 3,483,004 A | 12/1969 | Bauer et al. |
| 3,619,212 A | 11/1971 | Mori et al. |
| 4,393,049 A * | 7/1983 | Horrobin .................... 424/643 |
| 4,999,207 A | 3/1991 | Buckholz, Jr. et al. |
| 5,013,574 A | 5/1991 | Hassel |
| 5,273,754 A * | 12/1993 | Mann .......................... 424/440 |
| 5,466,459 A * | 11/1995 | Wilson ........................ 424/407 |
| 6,022,718 A | 2/2000 | Iwai et al. |
| 6,069,147 A * | 5/2000 | Williams et al. ............ 514/269 |
| 6,620,440 B1 | 9/2003 | Hsia et al. |
| 2002/0028257 A1 | 3/2002 | Chris et al. |
| 2002/0192308 A1* | 12/2002 | Mamana ..................... 424/729 |
| 2003/0104081 A1 | 6/2003 | Rombi |
| 2006/0035944 A1* | 2/2006 | Muto et al. ................. 514/365 |

FOREIGN PATENT DOCUMENTS

| CN | 1304682 A | | 7/2001 |
| CN | 1559410 A | * | 1/2005 |
| EP | 0 201 041 A | | 11/1986 |
| EP | 0 201 041 A1 | | 11/1986 |
| FR | 2 776 189 A | | 9/1999 |
| FR | 2776189 | | 9/1999 |
| GB | 1 201 650 A | | 8/1970 |
| GB | 1201650 | | 8/1970 |
| GB | 2 367 493 B | | 4/2002 |
| GB | 2367493 A | * | 4/2002 |
| JP | 2000-72642 A | | 3/2000 |
| JP | 2001-064672 | | 3/2001 |
| JP | 2001064672 A | * | 3/2001 |
| WO | WO 97/33599 A | | 9/1997 |
| WO | WO 97/33599 A1 | | 9/1997 |
| WO | WO 98/47376 A | | 10/1998 |
| WO | WO 98/47376 A1 | | 10/1998 |
| WO | WO 00/41708 A | | 7/2000 |
| WO | WO 00/41708 A1 | | 7/2000 |

OTHER PUBLICATIONS

Database WPI, Derwent Publications, Ltd., Class D13, XP-002256558 & CN 1 304 682, Jul. 25, 2001, Abstract.
Database WPI, Derwent Publications, Ltd., Class B04, XP-002285380 & JP 2000-072642, Mar. 7, 2000, Abstract.
Yeoh et al., "How does chili cause upper gastrointestinal symptoms? A correlation study with esophageal mucosal sensitivity and esophageal motility," J. Clin. Gastroenterol., 1995, 21, pp. 87-90 (Abstract).
Yoshioka et al., "Effects of red pepper added to high-fat and high-carbohydrate meals on energy metabolism and substrate utilization in Japanese women," British Journal of Nutrition, 1998, vol. 80, pp. 503-510.
Can Am Ingredients, Inc., "Soy Protein Isolates—Specification", Mgmt. Sys. ISO 9001:2000 Registered (1 page).
Naguib, "Soft Gel Capsules: An Elegant & Versatile Dosage Form," *Supplement Industry Executive*, (6 pgs.), Jul. 2002.
Rios-Estepa et al., "A systems biology approach identifies the biochemical mechanisms regulating monoterpenoid essential oil composition in peppermit," *PNAS*, vol. 105, No. 8, Feb. 26, 2008, pp. 2818-2823.
Mistry et al., "Prooxidant Effects of Monoglycerides and Disglycerides in Soybean Oil," *Journal of Food Science*, vol. 53, No. 6, 1998, pp. 1896-1897.
Halvarson et al., "A Method to Determine the Monoglyceride Content in Fats and Oils," *Journal of the American Oil Chemists' Society*, vol. 51, Apr. 1974, pp. 162-165.
184.1329 Glyceryl palmitosterate, *Code of Federal Regulations*, Title 21, vol. 3, revised as of Apr. 1, 2006.
Edwards, "Healthy North Dakota Oils: Agriculture to Health," *NDSU Extension Service*, North Dakota State University, Aug. 2005 (Reviewed and Reprinted Jun. 2007).
Aoyama et al., "Effect of Soy and Milk Whey Protein Isolates and Their Hydrolysats on Weight Reduction in Genetically Obese Mice," *Biosci. Biotechnol. Biochem.*, vol. 64, No. 12, 2000, pp. 2594-2600.
German Commission E monographs for Peppermint leaf, *American Botanical Council*, published Nov. 30, 1985 (Revised Mar. 13, 1990 and Sep. 1, 1990).
German Commission E monographs for Peppermint oil, *American Botanical Council*, published Mar. 13, 1986 (Revised Mar. 13, 1990, Sep. 1, 1990, and Jul. 14, 1993).
Pittler, M., et al.; "Dietary supplements for body-weight reduction: a systematic revew[1,2]"; Am J Clin Nutr (2004); 79:529-536.

* cited by examiner

Primary Examiner—Qiuwen Mi
(74) Attorney, Agent, or Firm—Foley & Lardner LLP

(57) ABSTRACT

A composition for oral administration containing capsaicinoids associated with a formulation base acceptable for oral administration, the formulation base comprising an oil and an additive solid or pasty at room temperature which represents 5 to 20 wt. %, preferably 8 to 15 wt. % of the composition.

13 Claims, No Drawings

COMPOSITION FOR ORAL ADMINISTRATION CONTAINING CAPSAICINOIDS

The present invention relates to a composition for oral administration containing capsaicinoids and to its use as medicament, food, food supplement or dietetic product. This composition has the advantage of having no irritant effect on the gastric mucosa.

The pimento fruit, fresh or dry, is generally used as a spice. Its piquancy which is experienced in the oral cavity is the result of its capsaicinoid content.

The capsaicinoids are mostly composed of capsaicin and to a minor extent of homocapsaicin and dihydrocapsaicin.

Scientific work which has been carried out for several years has demonstrated that the capsaicinoids which are present in pimento (or *capsicum*) are capable of stimulating thermogenesis.

Thermogenesis is the continuous regular development of heat in live organisms. One of the currently accepted pharmacological methods for the treatment and prevention of obesity is the stimulation of thermogenesis, which leads to an increase in energy expenditure and thus a higher consumption of calories.

An increase in thermogenesis by the known capsaicinoids in pimento is linked to a stimulation of the sympathic system. The metabolic aspect of this increase in thermogenesis differs according to the studies. In some studies it is linked to an increase in lipid oxidation. In other studies it is linked to the increase in sugar oxidation. Nevertheless, if the meal is rich in lipids, the oxidation of the latter becomes predominant.

The capability of the capsaicinoids found in pimento to stimulate thermogenesis and favor the oxidation of lipids is very interesting for avoiding the storage of fats and favoring the elimination of those which are already stored. It has also been observed that this increase in thermogenesis by the capsaicinoids found in pimento is accompanied by a reduced appetite.

Moreover, pimento is traditionally used for treating circulatory problems, in particular hypercholesterolemia, or certain digestive problems such as flatulence, gastric ulcers, gastroesophageal reflux and intestinal infections.

However, pimento frequently has the disadvantage of irritating the gastric mucosa.

The study of Yeoh K. G. et al. "How does chilli cause upper gastrointestinal symptoms" J. Clin. Gastroenterol., 1995, 21, p. 87-90 demonstrates that pain in the digestive tract which is brought about by ingestion of 5 g pimento comprising 0.048% by weight capsaicinoids could be linked to the stimulation of nerve endings located in the oesophagus.

People in Europe and the United States seem to be even more sensitive to the gastric-mucosa-irritating characteristics of this spice than people in Asia since the former consume much less pimento.

The problem of the irritation of the gastric mucosa, caused by pimento, thus limits the administration of capsaicinoids by oral administration.

To reduce the sensation of heat which can be brought about by pimento after ingestion, U.S. Pat. No. 5,273,754 proposes to combine it with a refreshing carminative such as peppermint, menthol, spearmint or carvone. However, these substances are highly odoriferous and can be annoying for people who do not like the taste of mint. It can also be desirable to have available a capsaicinoid-based composition without aroma or odor.

According to Reilly, C. A. (2001), the capsaicinoid content of fresh pimento varies from 0.01 to 510 µg/g. The oleoresin (or *capsicum* resin) is an organic pimento extract which is widely used in the food industry for aromatizing industrially made dishes. It can be used to impart a spicy taste in a reproducible manner and in concentrated form.

Since the oleoresin is lipophilic, the oils which are acceptable for oral administration are well adapted for the formulation of capsaicinoids.

The inventors have entirely surprisingly discovered that, by incorporating, into this oil, a lipophilic additive which is solid or pasty at room temperature, the resulting composition lacked any irritant effect on the gastric mucosa.

The present invention relates to a composition for oral administration containing capsaicinoids in combination with a formulation base which is acceptable for oral administration, said formulation base comprising an oil and a lipophilic additive which is solid or pasty at room temperature.

A formulation base is understood as meaning an inert support substance into which active elements are introduced.

The composition according to the invention is advantageously presented in a form which is solid or pasty at room temperature.

The lipophilic additive represents advantageously 5 to 20% by weight, preferably 8 to 15% by weight, of the composition.

The lipophilic additive advantageously has a melting point of between 30 and 80° C. so that it is solid or pasty at room temperature and can be melted in the oil using industrial standard equipment.

The lipophilic additive is preferably selected from among waxes, fatty acid mono-, di- or triglycerides, fatty acids and polyethylene glycols and the polyethylene glycol fatty acid esters, as well as their mixtures.

The waxes can be beeswax, candelilla wax, carnauba wax, polyethylene oxide wax or petroleum wax (or microcrystalline wax). Beeswax is advantageously used.

The fatty acid mono-, di- or triglycerides can have different degrees of esterification. Glycerol palmitostearate is advantageously used.

The fatty acids can be selected from among palmitic acid, stearic acid or behenic acid and their calcium, sodium, potassium or magnesium salts.

The polyethylene glycols and fatty acid polyethylene glycol esters advantageously have a molecular weight of between 600 to 6000.

The lipophilic additive is preferably composed of a mixture of beeswax and glycerol palmitostearate, with a preferred weight ratio of around 1.

Pimento is the fruit of an annual herbaceous plant from the family Solanaceae. The two species most widely used are *Capsicum annuum* and *Capsicum frutescens*, which are cultured in particular in Europe, in Africa and in North and South America.

Besides the capsaicinoids, pimento fruits contain carotenoids such as beta-carotene, zeaxanthin, violaxanthin, capsanthin and capsorubin (the 2 latter being specific of the genus *Capsicum*).

The capsaicinoids can be incorporated into the composition in the form of a powder of the dried fruit or the *capsicum* resin (or oleoresin).

*Capsicum* resin can contain between 3 and 50% by weight, preferably between 5 and 20% by weight, capsaicinoids.

The capsaicinoids are advantageously incorporated into the composition in the form of *capsicum* resin.

The capsaicinoids advantageously amount to between 0.02 and 5% by weight, preferably 0.1 to 2% by weight, of the composition.

The oil is advantageously selected from among the vegetable oils such as soya oil, sunflower oil, corn oil, olive oil or nut oil, and among the mineral oils such as liquid paraffin, as well as their mixtures.

The composition advantageously comprises one or more physiologically active components other than the capsaicinoids.

These other physiologically active components advantageously amount to 10 to 30% by weight of the composition and can be selected among thermogenesis or transit stimulators.

Scientific work which has been carried out for several years has demonstrated that certain foods are capable of stimulating thermogenesis: this is especially the case with caffeine, which is found in coffee and tea. Also, *Ascophyllum nodosum* is a transit stimulator.

At least one among the other physiologically active components is advantageously a plant or plant extract selected from among green tea, the alga *Ascophyllum nodosum*, mate tea, guarana, ephedra or citrus aurantium, as well as their mixtures, and/or a sunflower oil which is rich in conjugated linoleic acid.

The composition according to the invention can be present in the form of a soft or hard capsule. The shell of soft or hard capsules is advantageously made of beef gelatin, fish gelatin, hydroxypropylmethylcellulose or another polymer of plant or animal origin.

Since hard capsules have no tight closure system, it is simply necessary to employ a procedure which makes them tight (bandaging or internal sealing).

The composition according to the present invention is prepared by traditional techniques which are known to the skilled worker:

1) The lipophilic additive is incorporated into the oil which is heated at a temperature sufficiently high to melt the lipophilic additive completely and obtain a homogeneous mixture,
2) After cooling to approximately 50° C., the other components such as the *capsicum* oleoresin and the components which are thermogenesis stimulators are incorporated into this mixture with stirring,
3) The mixture thus obtained is cooled to a temperature between 25 and 40° C.,
4) Optionally, soft or hard capsules are filled with this mixture.

As formulated, the composition which the present invention relates to advantageously shows no sedimentation whatsoever of the other components which are stimulators of thermogenesis, such as green tea extract, or else transit stimulator such as powder of alga *Ascophyllum*.

The present invention also relates to the use of the composition as foodstuff, food supplement or dietetic product (a foodstuff intended for a particular diet).

In particular, the composition can be incorporated into foodstuffs which are industrially produced or craftsmen-prepared, such as oils, butter, margarine, bread spreads, chocolate. It can also be presented in the form of a powder for dilution in water or food bars.

The composition according to the present invention is advantageously used for stimulating thermogenesis, if appropriate together with a reduction of the appetite, without having an irritating effect on the gastric mucosa.

Advantageously, the composition of the present invention can thus be used for reducing or preventing the appearance of cellulite, or for reducing or preventing excess weight.

Very advantageously, the composition according to the present invention can be used as a food supplement for persons who wish to reduce their body fat by reducing the storage of food fats and eliminating more fats.

The present invention likewise relates to the use of the composition as medicament.

It is advantageously used for stimulating thermogenesis, if appropriate together with a reduction of the appetite, without having an irritating effect on the gastric mucosa.

Thus, it allows the treatment or prevention of obesity, circulation problems or certain digestive problems such as flatulence, gastric ulcers, gastroesophageal reflux and intestinal infections.

It can likewise be used for the symptomatic treatment of shingles, rheumatic pain, diabetes-related neuropathies and psoriasis.

A) Examples of Compositions in the Form of Soft Capsules

Compositions in the form of soft capsules were prepared from *capsicum* oleoresin, soya oil and approximately 5% by weight of beeswax and approximately 5% by weight of glycerol palmitostearate.

Formulation 1:
  15 mg *capsicum oleoresin*,
  150 mg green tea extract,
  75 mg sunflower oil which is rich in conjugated linoleic acid,
  200 mg soya oil,
  16 mg soya lecithin,
  29 mg yellow beeswax,
  25 mg glycerol palmitostearate,
  Shell of the soft capsule: gelatin, glycerol, sorbitol colorants.

Formulation 2:
  15 mg *capsicum oleoresin*,
  150 mg *Ascophyllum nodosum* powder,
  75 mg sunflower oil which is rich in conjugated linoleic acid,
  200 mg soya oil,
  16 mg soya lecithin,
  29 mg yellow beeswax,
  25 mg glycerol palmitostearate,
  Shell of the soft capsule: gelatin, glycerol, sorbitol colorants.

Formulations 1 and 2 were prepared as follows:
1) Melt the beeswax and the glycerol palmitostearate in the soya oil, heated to approximately 60° C.,
2) Cool the above mixture to approximately 50° C. and incorporate, with stirring, the rich-CLA sunflower oil, the soya lecithin, the *capsicum oleoresin* and the green tea extract or the *Ascophyllum nodosum*,
3) Cool the mixture to a temperature of between 25 and 40° C.,
4) Then fill soft capsules in the traditional manner.

Formulations 1 and 2 are presented in a form which is pasty at room temperature.

In a study carried out on women, Yoshioka M. et al. "Effects of red pepper added to high fat and high carbohydrate meals on energy metabolism" Br. J. Nut., 1998, No. 80, p. 503-510, the authors put forward the hypothesis that the metabolic response to the uptake of *Capsicum* differs between men and women.

In fact, women's muscles contain a higher percentage of type 1 fibers than men. These type 1 fibers comprise 3 times more beta-adrenergic receptors than the type 2 fibers. This difference will explain that, in this study, the metabolic response in women leads to a much higher level of lipid oxidation than in men.

Formulation 1 contains a green tea extract which is rich in caffeine, which is a stimulant of the beta-adrenergic system. This is why formulation 1 will be used advantageously for men.

B) In Vitro Tests on the Release of the Contents from the Soft Capsule

These tests were carried out with formulation 1 with the aid of an apparatus which measures the dissolution time (apparatus with rotating paddle), which is described in the European Pharmacopoeia.

The soft capsules are placed into 1000 ml of water with a temperature of 37° C.

The following results were obtained:

| Beeswax (% by weight based on the total composition) | Glycerol palmitostearate (% by weight based on the total composition) | Filling of the soft capsules | Dissolution time |
|---|---|---|---|
| 2% | 0% | OK | Release complete in less than 30 minutes |
| 3% | 0% | OK | |
| 4% | 0% | OK | |
| 5% | 0% | OK | |
| 6% | 0% | Too viscous for filling soft capsules | — |
| 5% | 3% | OK | Release complete in 90 minutes |
| 5% | 6% | Too viscous for filling soft capsules | — |
| 5% | 5% | OK | Release complete in 120 minutes |

These results show that the in vitro dissolution times of the compositions depend on the ratio of beeswax and glycerol palmitostearate.

Certain ratios lead to a rise in the melting point of the mixture. Therefore, the temperature at which the oily mixture is filled into the soft capsule becomes too high to allow the soft capsules to be filled.

Complete dissolution in approximately 120 minutes is obtained with a composition comprising 5% by weight of beeswax and 5% by weight of glycerol palmitostearate.

The minimum desirable dissolution time is at least 1 hour. It is preferably at least 90 minutes, more preferably at least 120 minutes.

C) Digestive Tolerance Tests on Healthy Subjects

The improvement of the digestive tolerance of *capsicum* by combining it with beeswax/glycerol palmitostearate was tested on 20 healthy subjects which took the following in succession and in random order:
  composition without wax and without glycerol palmitostearate,
  for women: composition 2; for men: composition 1.

| | Percentage of subjects with digestive tolerance problems such as stomach pains and sensations of burning | Percentage of subjects with good digestive tolerance |
|---|---|---|
| Composition without wax and without glycerol palmitostearate | 55% | 45% |
| Composition comprising 5% by weight of beeswax and 5% by weight of glycerol palmitostearate | 0% | 100% |

This test shows that the compositions comprising a mixture of beeswax and glycerol palmitostearate as lipophilic additive which is solid or pasty at room temperature lead, for the same dose of *capsicum oleoresin*, to less burning in the digestive tract than the soft capsules which comprise no lipophilic additive which is solid or pasty at room temperature.

The invention claimed is:

1. An oral composition for stimulating thermogenesis comprising capsaicinoids in combination with a formulation base which is acceptable for oral administration, said formulation base consisting essentially of:
  at least one vegetable and/or mineral oil selected from soya oil, sunflower oil, corn oil, olive oil, nut oil, and a liquid paraffin;
  and lipophilic additives of:
    a) approximately 5% by weight of beeswax based on the total weight of the composition;
    b) approximately 5% by weight of glycerol palmitostearate based on the total weight of the composition; and
    c) approximately 0% to 10% by weight of a lipophilic additive selected from the group consisting of polyethylene glycol, candelilla wax, carnauba wax, polyethylene oxide wax, and petroleum wax,
  wherein the composition is a dosage form chosen between soft or hard capsules.

2. The composition of claim 1, wherein the capsaicinoids are present in the composition as capsicum resin.

3. The composition of claim 1, wherein the capsaicinoids represent 0.02 to 5% by weight of the composition.

4. The composition of claim 1, wherein the vegetable oil is selected from soya oil, sunflower oil, and a mixture thereof.

5. The composition of claim 1, wherein the composition comprises one or more physiologically active components other than the capsaicinoids.

6. The composition of claim 3, wherein the capsaicinoids represent 0.1 to 2% by weight of the composition.

7. The composition of claim 5, wherein the other physiologically active component(s) amount to 10 to 30% by weight of the composition.

8. The composition of claim 5, wherein at least one among the other physiologically active components is a plant or a plant extract selected from green tea, alga *Ascophyllum nodosum*, mate tea, guarana, ephedra, citrus aurantium, and mixtures thereof 9. A method for stimulating thermogenesis comprising administering the composition as claimed in claim 1 to a subject in need thereof.

10. The method as claimed in claim 9, for stimulating thermogenesis without exerting an irritant effect on the gastric mucosa.

11. The method as claimed in claim 9, for additionally reducing the appetite.

12. The method as claimed in claim 9, for treating obesity, digestive problems, circulation problems, or hypercholesterolemia, or for reducing the appearance of cellulite.

13. The method as claimed in claim 12, wherein said digestive problems are flatulence, gastric ulcers, gastroesophageal reflux and intestinal infections.

* * * * *